United States Patent [19]

Berry

[11] Patent Number: 4,544,503
[45] Date of Patent: Oct. 1, 1985

[54] PROCESS FOR PRODUCING ACYLOXYBENZENESULFONATE SALTS

[75] Inventor: C. Bernard Berry, Baton Rouge, La.

[73] Assignee: Ethyl Corporation, Richmond, Va.

[21] Appl. No.: 528,456

[22] Filed: Sep. 1, 1983

[51] Int. Cl.$^4$ .................. C07C 143/90; C11D 1/28
[52] U.S. Cl. ............................. 260/402; 560/142
[58] Field of Search ............ 260/402, 410.9 C; 560/142

[56] References Cited

U.S. PATENT DOCUMENTS

| 2,125,072 | 7/1938 | Kern | 260/402 X |
| 2,467,206 | 4/1949 | Gresham et al. | 560/130 |
| 2,542,767 | 2/1951 | Gresham et al. | 260/410.9 C X |
| 3,168,553 | 2/1965 | Slaugh | 260/410.9 C X |
| 3,507,891 | 4/1970 | Hearne et al. | 260/410.9 C |
| 3,660,439 | 5/1972 | Schell | 260/410.9 C |

Primary Examiner—Helen M. S. Sneed
Attorney, Agent, or Firm—Donald L. Johnson; John F. Sieberth; Joseph D. Odenweller

[57] ABSTRACT

A method of preparing alkali metal salts or alkaline earth metal salts of acyloxybenzenesulfonate by reacting an alkali metal salt or an alkaline earth metal salt of hydroxybenzenesulfonic acid with an organic compound containing olefinic unsaturation and carbon monoxide at elevated temperature and elevated pressure in the presence of a catalytic amount of a metal carbonyl compound and a promoter selected from pyridine, non-ortho-substituted alkylpyridine or mixtures thereof.

17 Claims, No Drawings

PROCESS FOR PRODUCING ACYLOXYBENZENESULFONATE SALTS

TECHNICAL FIELD

This invention relates to the production of alkali metal salts and alkaline earth metal salts of certain acyloxybenzenesulfonates, and more particularly, to the manufacture of these salts by the reaction between the corresponding salts of hydroxybenzenesulfonic acid, carbon monoxide and an olefinically unsaturated hydrocarbon in the presence of a catalyst consisting of a metal carbonyl compound and a promoter selected from pyridine, non-ortho-substituted alkylpyridine or mixtures thereof. The acyloxybenzenesulfonate salts of the present invention have many applications. For example, they are used in the textile industry as activators for the peroxide bleaching of fabrics and as dyeing assistants in the dyeing of acrylic fibers.

THE INVENTION

According to the process of the present invention, an olefinically unsaturated compound is carbonylated by contacting the olefinic reactant with carbon monoxide and an alkali metal salt or an alkaline earth metal salt of hydroxybenzenesulfonic acid in the presence of a catalyst composition as herein described at elevated temperature and elevated pressure. By the process of this invention, alkali metal salts and alkaline earth metal salts of acyloxybenzenesulfonate are produced in relatively high yields and with a relatively high ratio of straight-chain to branched chain products.

In a specific embodiment, and by way of illustration, the present invention contemplates the production of sodium 4-nonanoyloxybenzenesulfonate in accordance with the following equation:

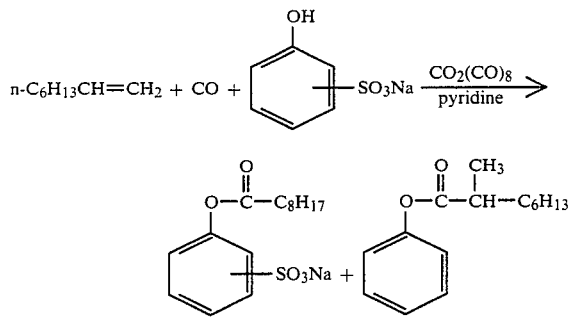

The olefinic unsaturated compounds which are used in the process of the invention are olefins, both straight-chain or branched alpha-olefins and olefins with an internal double bond. Moreover, olefins with more than one double bond and those with specific substituents, for instance, aryl groups, are also suitable.

As a rule, olefins having 2 to about 40, preferably 4–20, and especially preferred olefins having 6–10 carbon atoms are used. These may be obtained by methods of the state of the art. For instance, alpha-olefins are obtained by Ziegler oligomerization of ethylene as disclosed in U.S. Pat. No. 3,310,600, or by wax cracking. Olefins with an internal double bond can be produced by dehydrogenation or by chlorination with ensuing dehydrochlorination of paraffins, as disclosed in British Pat. No. 1,037,868.

As regards the last cited method, blends of pariffins are used as a rule, i.e., mixtures of different carbon numbers, whereby the olefins that are obtained in turn also lack a uniform carbon number.

Moreover and naturally, all conceivable linear isomeric forms are present in these olefins mixtures. Besides the use of pure and possibly substituted olefins, it is also possible to use olefin mixtures having a paraffin content, for example, of up to about 85% by weight. This paraffin content results because complete conversion is not achieved in the production of olefins, and the unconverted paraffins are not separated, or are only incompletely separated.

The hydroxybenzenesulfonate salts which may be used in accordance with this invention are salts of the formula:

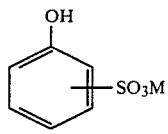

wherein M is an alkali metal or an alkaline earth metal. The metal sulfonate functional group can be bonded to any of the aromatic carbon atoms either ortho-, meta- or para- to the hydroxyl group in the ring. The hydroxybenzenesulfonate salts of the present invention are known compounds and can be prepared by methods known to the art, such as, for example, by treating phenol with sulfuric acid in the presence of boron fluoride at elevated temperature as described by R. J. Thomas, et al., "Sulfonation and Nitration Reaction Promoted by Boron Fluoride", *Industrial and Engineering Chemistry*, 32, 408–410 (1940).

Representative examples of hydroxybenzenesulfonate salt reactants which can be used in the present process include:
sodium 2-hydroxybenzenesulfonate;
sodium 3-hydroxybenzenesulfonate;
sodium 4-hydroxybenzenesulfonate;
potassium 2-hydroxybenzenesulfonate;
potassium 3-hydroxybenzenesulfonate;
potassium 4-hydroxybenzenesulfonate;
calcium 2-hydroxybenzenesulfonate;
calcium 3-hydroxybenzenesulfonate; and
calcium 4-hydroxybenzenesulfonate.

Representative examples of acyloxybenzenesulfonate salt products which can be made by the present process include:
benzenesulfonic acid, 2-hydroxy-,propionate,sodium salt;
benzenesulfonic acid, 2-hydroxy-,propionate,potassium salt;
benzenesulfonic acid, 2-hydroxy-,propionate,calcium salt;
benzenesulfonic acid, 3-hydroxy-,propionate,sodium salt;
benzenesulfonic acid, 3-hydroxy-,propionate,potassium salt;
benzenesulfonic acid, 3-hydroxy-,propionate,calcium salt;
benzenesulfonic acid, 4-hydroxy-,propionate,sodium salt;
benzenesulfonic acid, 4-hydroxy-,propionate,potassium salt;

benzenesulfonic acid, 4-hydroxy-,propionate,calcium salt;
benzenesulfonic acid, 4-hydroxy-,butyrate,sodium salt;
benzenesulfonic acid, 4-hydroxy-,pentanoate,sodium salt;
benzenesulfonic acid, 4-hydroxy-,hexanoate,sodium salt;
benzenesulfonic acid, 2-hydroxy-,heptanoate,sodium salt;
benzenesulfonic acid, 2-hydroxy-,heptanoate,potassium salt;
benzenesulfonic acid, 2-hydroxy-,heptanoate,calcium salt;
benzenesulfonic acid, 3-hydroxy-,heptanoate,sodium salt;
benzenesulfonic acid, 3-hydroxy-,heptanoate,potassium salt;
benzenesulfonic acid, 3-hydroxy-,heptanoate,calcium salt;
benzenesulfonic acid, 4-hydroxy-,heptanoate,sodium salt;
benzenesulfonic acid, 4-hydroxy-,heptanoate,potassium salt;
benzenesulfonic acid, 4-hydroxy-,heptanoate,calcium salt;
benzenesulfonic acid, 4-hydroxy-,octanoate,sodium salt;
benzenesulfonic acid, 2-hydroxy-,nonanoate,sodium salt;
benzenesulfonic acid, 2-hydroxy-,nonanoate,potassium salt;
benzenesulfonic acid, 2-hydroxy-,nonanoate,calcium salt;
benzenesulfonic acid, 3-hydroxy-,nonanoate,sodium salt;
benzenesulfonic acid, 3-hydroxy-,nonanoate,potassium salt;
benzenesulfonic acid, 3-hydroxy-,nonanoate,calcium salt;
benzenesulfonic acid, 4-hydroxy-,nonanoate,sodium salt;
benzenesulfonic acid, 4-hydroxy-,nonanoate,potassium salt;
benzenesulfonic acid, 4-hydroxy-,nonanoate,calcium salt;
benzenesulfonic acid, 4-hydroxy-,decanoate,sodium salt;
benzenesulfonic acid, 4-hydroxy-,undecanoate,sodium salt;
benzenesulfonic acid, 4-hydroxy-,dodecanoate,sodium salt;
benzenesulfonic acid, 4-hydroxy-,tridecanoate,sodium salt;
benzenesulfonic acid, 4-hydroxy-,tetradecanoate,-sodium salt;
benzenesulfonic acid, 4-hydroxy-,pentadecanoate,-sodium salt;
benzenesulfonic acid, 4-hydroxy-,hexadecanoate,-sodium salt;
benzenesulfonic acid, 4-hydroxy-,heptadecanoate,-sodium salt;
benzenesulfonic acid, 4-hydroxy-,octadecanoate,-sodium salt;
benzenesulfonic acid, 4-hydroxy-,nonadecanoate,-sodium salt;
benzenesulfonic acid, 4-hydroxy-,eicosanoate,sodium salt;
benzenesulfonic acid, 4-hydroxy-,heneicosanoate,-sodium salt;
benzenesulfonic acid, 4-hydroxy-,docosanoate,sodium salt;
benzenesulfonic acid, 4-hydroxy-,tricosanoate,sodium salt;
benzenesulfonic acid, 4-hydroxy-,tetracosanoate,-sodium salt;
benzenesulfonic acid, 4-hydroxy-,pentacosanoate,-sodium salt;
benzenesulfonic acid, 4-hydroxy-,hexacosonoate,-sodium salt;
benzenesulfonic acid, 4-hydroxy-,heptacosanoate,-sodium salt;
benzenesulfonic acid, 4-hydroxy-,octacosanoate,sodium salt;
benzenesulfonic acid, 4-hydroxy-,nonacosonoate,-sodium salt;
benzenesulfonic acid, 4-hydroxy-,triacontanoate,-sodium salt;
benzenesulfonic acid, 4-hydroxy-,pent-2-enoate,sodium salt;
benzenesulfonic acid, 4-hydroxy-,pent-2-enoate,potassium salt;
benzenesulfonic acid, 4-hydroxy-,pent-2-enoate,calcium salt;
benzenesulfonic acid, 4-hydroxy-,pent-3-enoate,sodium salt;
benzenesulfonic acid, 4-hydroxy-,pent-3-enoate,potassium salt;
benzenesulfonic acid, 4-hydroxy-,pent-3-enoate,calcium salt;
benzenesulfonic acid, 4-hydroxy-,hex-2-enoate,sodium salt;
benzenesulfonic acid, 4-hydroxy-,hex-3-enoate,sodium salt;
benzenesulfonic acid, 4-hydroxy-,hex-4-enoate,sodium salt;
benzenesulfonic acid, 4-hydroxy-,hex-5-enoate,sodium salt;
benzenesulfonic acid, 4-hydroxy-,hept-2-enoate,sodium salt;
benzenesulfonic acid, 4-hydroxy-,hept-3-enoate,sodium salt;
benzenesulfonic acid, 4-hydroxy-,hept-4-enoate,sodium salt;
benzenesulfonic acid, 4-hydroxy-,hept-5-enoate,sodium salt;
benzenesulfonic acid, 4-hydroxy-,hept-6-enoate,sodium salt;
benzenesulfonic acid, 4-hydroxy-,oct-2-enoate,sodium salt;
benzenesulfonic acid, 4-hydroxy-,oct-3-enoate,sodium salt;
benzenesulfonic acid, 4-hydroxy-,oct-4-enoate,sodium salt;
benzenesulfonic acid, 4-hydroxy-,non-2-enoate,sodium salt;
benzenesulfonic acid, 4-hydroxy-,non-3-enoate,sodium salt;
benzenesulfonic acid, 4-hydroxy-,non-4-enoate,sodium salt;
benzenesulfonic acid, 4-hydroxy-,dec-2-enoate,sodium salt;
benzenesulfonic acid, 4-hydroxy-,dec-3-enoate,sodium salt;
benzenesulfonic acid, 4-hydroxy-,dec-4-enoate,sodium salt;

benzenesulfonic acid, 4-hydroxy-,undec-2-enoate,-sodium salt;
benzenesulfonic acid, 4-hydroxy-,undec-3-enoate,-sodium salt;
benzenesulfonic acid, 4-hydroxy-,undec-4-enoate,-sodium salt;
benzenesulfonic acid, 4-hydroxy-,dodec-2-enoate,-sodium salt;
benzenesulfonic acid, 4-hydroxy-,dodec-3-enoate,-sodium salt;
benzenesulfonic acid, 4-hydroxy-,dodec-4-enoate,-sodium salt;
benzenesulfonic acid, 4-hydroxy-,tridec-2-enoate,-sodium salt;
benzenesulfonic acid, 4-hydroxy-,tridec-3-enoate,-sodium salt;
benzenesulfonic acid, 4-hydroxy-,tridec-4-enoate,-sodium salt;
benzenesulfonic acid, 4-hydroxy-,tetradec-2-enoate,-sodium salt;
benzenesulfonic acid, 4-hydroxy-,tetradec-3-enoate,-sodium salt;
benzenesulfonic acid, 4-hydroxy-,tetradec-4-enoate,-sodium salt;
benzenesulfonic acid, 4-hydroxy-,pentadec-2-enoate,-sodium salt;
benzenesulfonic acid, 4-hydroxy-,pentadec-3-enoate,-sodium salt;
benzenesulfonic acid, 4-hydroxy-,pentadec-4-enoate,-sodium salt;
benzenesulfonic acid, 4-hydroxy-,hexadec-2-enoate,-sodium salt;
benzenesulfonic acid, 4-hydroxy-,hexadec-3-enoate,-sodium salt;
benzenesulfonic acid, 4-hydroxy-,hexadec-4-enoate,-sodium salt;
benzenesulfonic acid, 4-hydroxy-,heptadec-2-enoate,-sodium salt;
benzenesulfonic acid, 4-hydroxy-,heptadec-3-enoate,-sodium salt;
benzenesulfonic acid, 4-hydroxy-,heptadec-4-enoate,-sodium salt;
benzenesulfonic acid, 4-hydroxy-,octadec-2-enoate,-sodium salt;
benzenesulfonic acid, 4-hydroxy-,octadec-3-enoate,-sodium salt;
benzenesulfonic acid, 4-hydroxy-,octadec-4-enoate,-sodium salt;
benzenesulfonic acid, 4-hydroxy-,nonadec-2-enoate,-sodium salt;
benzenesulfonic acid, 4-hydroxy-,nonadec-3-enoate,-sodium salt;
benzenesulfonic acid, 4-hydroxy-,nonadec-4-enoate,-sodium salt;
benzenesulfonic acid, 4-hydroxy-,eicos-2-enoate,sodium salt;
benzenesulfonic acid, 4-hydroxy-,eicos-3-enoate,sodium salt;
benzenesulfonic acid, 4-hydroxy-,eicos-4-enoate,sodium salt;
benzenesulfonic acid, 4-hydroxy-,heneicos-2-enoate,-sodium salt;
benzenesulfonic acid, 4-hydroxy-,heneicos-3-enoate,-sodium salt;
benzenesulfonic acid, 4-hydroxy-,heneicos-4-enoate,-sodium salt;
benzenesulfonic acid, 4-hydroxy-,docos-2-enoate,-sodium salt;
benzenesulfonic acid, 4-hydroxy-,docos-3-enoate,-sodium salt;
benzenesulfonic acid, 4-hydroxy-,docos-4-enoate,-sodium salt;
benzenesulfonic acid, 4-hydroxy-,tricos-2-enoate,-sodium salt;
benzenesulfonic acid, 4-hydroxy-,tricos-3-enoate,-sodium salt;
benzenesulfonic acid, 4-hydroxy-,tricos-4-enoate,-sodium salt;
benzenesulfonic acid, 4-hydroxy-,tetracos-2-enoate,-sodium salt;
benzenesulfonic acid, 4-hydroxy-,tetracos-3-enoate,-sodium salt;
benzenesulfonic acid, 4-hydroxy-,tetracos-4-enoate,-sodium salt;
benzenesulfonic acid, 4-hydroxy-,pentacos-2-enoate,-sodium salt;
benzenesulfonic acid, 4-hydroxy-,pentacos-3-enoate,-sodium salt;
benzenesulfonic acid, 4-hydroxy-,pentacos-4-enoate,-sodium salt;
benzenesulfonic acid, 4-hydroxy-,hexacos-2-enoate,-sodium salt;
benzenesulfonic acid, 4-hydroxy-,hexacos-3-enoate,-sodium salt;
benzenesulfonic acid, 4-hydroxy-,hexacos-4-enoate,-sodium salt;
benzenesulfonic acid, 4-hydroxy-,heptacos-2-enoate,-sodium salt;
benzenesulfonic acid, 4-hydroxy-,heptacos-3-enoate,-sodium salt;
benzenesulfonic acid, 4-hydroxy-,heptacos-4-enoate,-sodium salt;
benzenesulfonic acid, 4-hydroxy-,octacos-2-enoate,-sodium salt;
benzenesulfonic acid, 4-hydroxy-,octacos-3-enoate,-sodium salt;
benzenesulfonic acid, 4-hydroxy-,octacos-4-enoate,-sodium salt;
benzenesulfonic acid, 4-hydroxy-,nonacos-2-enoate,-sodium salt;
benzenesulfonic acid, 4-hydroxy-,nonacos-3-enoate,-sodium salt;
benzenesulfonic acid, 4-hydroxy-,nonacos-4-enoate,-sodium salt;
benzenesulfonic acid, 4-hydroxy-,triacont-2-enoate,-sodium salt;
benzenesulfonic acid, 4-hydroxy-,triacont-3-enoate,-sodium salt;
benzenesulfonic acid, 4-hydroxy-,triacont-4-enoate,-sodium salt;
benzenesulfonic acid, 4-hydroxy-,phenylpropionate,-sodium salt;
benzenesulfonic acid, 4-hydroxy-,phenylpropionate,-potassium salt;
benzenesulfonic acid, 4-hydroxy-,phenylpropionate,calcium salt;
benzenesulfonic acid, 4-hydroxy-,phenylbutyrate,-sodium salt;
benzenesulfonic acid, 4-hydroxy-,phenylpentanoate,-sodium salt;
benzenesulfonic acid, 4-hydroxy-,phenylhexanoate,-sodium salt;
benzenesulfonic acid, 4-hydroxy-,phenylheptanoate,-sodium salt;
benzenesulfonic acid, 4-hydroxy-,phenyloctanoate,-sodium salt;

benzenesulfonic acid, 4-hydroxy-,phenylnonanoate,- sodium salt;
benzenesulfonic acid, 4-hydroxy-,phenyldecanoate,- sodium salt;
benzenesulfonic acid, 4-hydroxy-,phenylundecanoate,- sodium salt;
benzenesulfonic acid, 4-hydroxy-,phenyldodecanoate,- sodium salt;
benzenesulfonic acid, 4-hydroxy-,phenyltridecanoate,- sodium salt;
benzenesulfonic acid, 4-hydroxy-,phenyltetradecanoate,sodium salt;
benzenesulfonic acid, 4-hydroxy-,phenylpentadecanoate,sodium salt;
benzenesulfonic acid, 4-hydroxy-,phenylhexadecanoate,sodium salt;
benzenesulfonic acid, 4-hydroxy-,phenylheptadecanoate,sodium salt;
benzenesulfonic acid, 4-hydroxy-,phenyloctadecanoate,sodium salt;
benzenesulfonic acid, 4-hydroxy-,phenylnonadecanoate,sodium salt;
benzenesulfonic acid, 4-hydroxy-,phenyleicosanoate,- sodium salt;
benzenesulfonic acid, 4-hydroxy-,cyclobutanecarboxylate,sodium salt;
benzenesulfonic acid, 4-hydroxy-,cyclopentanecarboxylate,sodium salt;
benzenesulfonic acid, 4-hydroxy-,cyclohexanecarboxylate,sodium salt;
benzenesulfonic acid, 4-hydroxy-,cycloheptanecarboxylate,sodium salt;
benzenesulfonic acid, 4-hydroxy-,cyclooctanecarboxylate,sodium salt;
benzenesulfonic acid, 4-hydroxy-,cyclononanecarboxylate,sodium salt;
benzenesulfonic acid, 4-hydroxy-,cyclodecanecarboxylate,sodium salt;
benzenesulfonic acid, 4-hydroxy-,cycloundecanecarboxylate,sodium salt;
benzenesulfonic acid, 4-hydroxy-,cyclododecanecarboxylate,sodium salt;
benzenesulfonic acid, 4-hydroxy-,cyclotridecanecarboxylate,sodium salt;
benzenesulfonic acid, 4-hydroxy-,cyclotetradecanecarboxylate, sodium salt;
benzenesulfonic acid, 4-hydroxy-,cyclopentadecanecarboxylate, sodium salt;
benzenesulfonic acid, 4-hydroxy-,cyclohexadecanecarboxylate, sodium salt;
benzenesulfonic acid, 4-hydroxy-,cycloheptadecanecarboxylate, sodium salt;
benzenesulfonic acid, 4-hydroxy-,cyclooctadecanecarboxylate, sodium salt;
benzenesulfonic acid, 4-hydroxy-,cyclononadecanecarboxylate, sodium salt;
benzenesulfonic acid, 4-hydroxy-,cycloeicosanecarboxylate,sodium salt; and mixtures thereof.

In the process described herein, metal carbonyl catalysts are used. These catalysts include particularly carbonyls of cobalt, iron, or nickel, such as iron-pentacarbonyl, dicobaltoctacarbonyl and nickel-tetracarbonyl. Dicobalt-octacarbonyl is very particularly suitable. These catalysts can be added to the medium in the solid state or in the form of a solution in a reaction solvent. The metal carbonyl compounds are usually employed in the present process in an amount ranging from about 1% to about 20% by weight based on the weight of the hydroxybenzenesulfonic acid salt reactant employed in the process. The metal carbonyl compounds used in the process may optionally be made in situ, for example, by reacting cobalt oxide with carbon monoxide and hydrogen in the presence of pyridine.

In addition to pyridine alone or in a mixture, other applicable promoters which can be used in the instant process include all non-ortho-substituted alkylpyridines such as 3-picoline, 4-picoline, 3,4-dimethylpyridine, 3,5-dimethylpyridine, 3-ethylpyridine and 4-ethylpyridine. Such promoters are used to the extent of about 1-50 moles, preferably from about 2-20 moles per 1 mol of the metal carbonyl catalyst compound. The use of a pyridine promoter has been found to maximize acyl group linearity in the acyloxybenzenesulfonate salt product.

The process of the invention can be conducted by any of a variety of procedures. In one modification, the olefinic reactant, the alkali metal salt or alkaline earth metal salt of hydroxybenzenesulfonic acid, the catalyst composition and carbon monoxide are charged to an autoclave or similar pressure reactor for operations in a batch-wise manner. In another modification, the reaction can be effected in a continuous operation as by contacting the entire reaction mixture during passge through a tubular reactor. It is equivalently useful to add the carbon monoxide continuously throughout the period of the reaction.

In the carbonylation process of the instant invention, one mole of carbon monoxide will be consumed for each mole of olefinic double bond carbonylated. However, generally an excess of carbon monoxide is present in the reaction environment. The carbon monoxide is generally of standard commercial quality and may contain inert impurities such as carbon dioxide, nitrogen, noble gases and paraffinic hydrocarbons having from 1 to 4 carbon atoms. Such impurities, should not, however, be present in great quantities since the size of the process equipment would be increased. When such impurities are present, the total reactor pressure will have to be increased to maintain the desired carbon monoxide partial pressure.

For each mole of olefinic double bond carbonylated, there also will be consumed 1 equivalent of hydroxybenzenesulfonic acid salt. Thus, in carbonylations involving olefin, carbon monoxide and hydroxybenzenesulfonic acid salt, there will be consumed 1 mole of hydroxybenzenesulfonic acid salt for each mole of olefinic double bond carbonylated. Although the relative proportions of reactants employed in the reaction may be the stoichiometrically required quantities, other proportions may be employed if desired. For example, an excess of either olefinic reactant or hydroxybenzenesulfonic acid salt reactant may be used in the reaction since the use of greater than stoichiometric quantities serves to drive the reaction to completion.

Due to the high activity of the catalyst compositions of the instant invention, operating conditions are relatively mild. Operating temperatures of from about 125° C. to about 200° C. are satisfactory with temperatures of from about 140° C. to 170° C. being preferred. The optimum temperature will depend upon the specific olefin reactant used as well as the particular hydroxybenzenesulfonic acid salt with which its is being carbonylated, the particular solvent, if any, used in the reaction and the particular pressure at which the reaction is carried out.

The carbonylations of this invention are conducted under carbon monoxide partial pressures of from about 500 psig to about 4000 psig, with carbon monoxide partial pressures of from about 800 psig to about 2000 psig being preferred.

Although not required, it is preferred that the process be carried out under substantially anhydrous conditions, and accordingly, the components of the reaction system are brought together and maintained under a substantially dry, inert atmosphere. It is not necessary, however, that the reagents used in the process be anhydrous before they are combined as any water present in the reagents can be removed therefrom by conversion techniques, such as, for example, by azeotriopic distillation of the combined reagents using an organic solvent such as hexane, octane, toluene, xylenes, and the like.

Although a solvent is not required in order to carry out the instant carbonylation reactions, especially if an excess of olefinic compound is used in the process to serve both as a reactant and a solvent, a solvent is often desired. Various organic solvents which may be employed for this purpose include carboxylic acids such as acetic acid, propionic acid, octanoic acid, the chlorinated benzenes, the chlorinated toluenes, high boiling alkanes such as undecane, tetradecane, hexadecane, mineral oil and mixtures of higher boiling linear and branched alkanes. Additionally, aprotic solvents such as triglyme, tetraglyme, 1,2-diethoxyethane, N,N-dimethylacidamide, dimethylsulfoxide, N,N-dimethylformamide, dimethylene sulfone, tetramethylene sulfone, N-methylpyrrolidone, acetonitrile and like materials also may be used. Further, ethers such as diethyl ether, dibutyl ether, 1-ethoxyhexane, and tetrahydrofuran may be used. Also, lower alkanols having up to about 6 carbon atoms including methanol, ethanol, n-propanol, isopropyl alcohol, n-butanol, sec-butyl alcohol, tert-butyl alcohol, n-pentanol, isopentyl alcohol, n-hexanol and isohexyl alcohol can be used as solvents in the process. Whenever a solvent is employed, the amount used is not critical and can vary widely. Typically, amounts of solvent of from about 10% to about 500% by weight of the total reactants are satisfactory.

Subsequent to the reaction, the reaction mixture can be separated by conventional means such as filtration followed by selective extraction, and the like. The product can be further purified as, for example, by recrystallization. Any unreacted olefinic and salt reactants as well as the catalyst composition can be recovered and recycled and further reacted by the process of this invention.

The following examples are presented to describe the invention more fully without any intention of being limited to the details thereof.

EXAMPLE 1

Preparation of Benzenesulfonic Acid, 4-Hydroxynonanoate, Sodium Salt

Into a 300 mL autoclave were placed 9.8 g sodium 4-hydroxybenzenesulfonate, 1.0 g dicobalt-octacarbonyl, 30 mLs 1-octene, 45 mLs acetonitrile and 5.1 mLs pyridine. The autoclave was then charged with carbon monoxide and pressurized to 750 psig of carbon monoxide. The autoclave was heated to 150° C. under 750–1200 psig carbon monoxide and maintained at these conditions for 2.5 hours. The pressure was then raised to 2000 psig and the reaction mixture was maintained at 2000 psig and 145° C. to 147° C. for 18 hours. The resultant mixture was then cooled to room temperature, vented and the solid reaction product was isolated by filtration and washed three times with diethyl ether to give 13.2 g of a purple solid. Analysis by cationic titration indicated that the product contained 73.6 weight percent benzenesulfonic acid, 4-hydroxynonanoate, sodium salt (58% yield).

EXAMPLE 2

Preparation of Benzenesulfonic Acid, 4-Hydroxynonanoate, Sodium Salt

Into a 300 mL autoclave were placed 9.8 g sodium 4-hydroxybenzenesulfonate, 1.0 g dicobalt-octacarbonyl, 18 mLs 1-octene, 60 mLs tetraglyme and 5.2 mLs pyridine. The autoclave was then charged with carbon monoxide and pressurized to 1200 psig. The autoclave was heated to 150° C. and the pressure was increased to 2000 psig. The reaction mixture was maintained at approximately 1900 psig and 150° C. for 17 hours. The resultant mixture was then cooled to room temperature, vented and taken up in xylene. The solid was separated by centrifugation and washed twice with diethyl ether and dried to give 9.1 g of a brown solid. Analysis by cationic titration indicated that the product contained 72.1 weight percent benzenesulfonic acid, 4-hydroxynonanoate, sodium salt (approximately 60% yield).

In a similar manner, several other runs were carried in which benzenesulfonic acid, 4-hydroxynonanoate, sodium salt was prepared and the solvent and reaction conditions were varied. The results are given in the Table below. Yields were determined by NMR unless otherwise stated.

TABLE

Benzenesulfonic Acid, 4-Hydroxynonanoate, Sodium Salt Preparation

| Run No. | 1-Octene (mmoles) | Sodium 4-Hydroxybenzene-Sulfonate Reactant (mmoles) | Dicobalt-Octacarbonyl (mmoles) | Pyridine (mmoles) | Solvent/Other Reagents | Temp. (°C.) | Pressure CO (psig) | Time (hrs.) | Product (mole %) |
|---|---|---|---|---|---|---|---|---|---|
| 3 | 320 | 100 | 2 | 64 | None | 150 | 2000 | 24 | 46 |
| 4 | 120 | 100 | 2 | None | triglyme (70 mLs) | 150 | 2000 | 19 | <5 |
| 5 | 320 | 100 | 3.2 | 148 | triglyme (20 mLs) | 150 | 2100 | 4 | ~15 |
| 6 | 320 | 100 | 2 | 64 | None | 180 | 2000 | 17 | ~5 |
| 7 | 250 | 100 | 5.8 | None | lutidine (125 mmoles) | 150 | 2000 | 24 | 11 |
| 8 | 320 | 100 | 5.8 | 128 | isopropanol (10 mmoles) | 150 | 2000 | 17 | 27[1] |
| 9 | 250 | 100 | 5.8 | 126 | acetonitrile (50 mLs) | 150 | 2000 | 17 | 48 |
| 10 | 96 | 50 | 5.8 | 126 | acetonitrile (100 mLs) | 150 | 2000 | 16 | 46 |

TABLE-continued

Benzenesulfonic Acid, 4-Hydroxynonanoate, Sodium Salt Preparation

| Run No. | 1-Octene (mmoles) | Sodium 4-Hydroxybenzene-Sulfonate Reactant (mmoles) | Dicobalt-Octacarbonyl (mmoles) | Pyridine (mmoles) | Solvent/Other Reagents | Temp. (°C.) | Pressure CO (psig) | Time (hrs.) | Product (mole %) |
|---|---|---|---|---|---|---|---|---|---|
| 11 | 250 | 50 | 2.9 | 64 | acetic acid (20 mLs) | 150 | 2000 | 18 | <5 |

(1)Yield was determined by cationic titration.

Having disclosed the process of the present invention, one skilled in the art can readily envision various modifications and changes which are nevertheless within the scope of the invention. Therefore, it is desired that the process of this invention be limited only by the lawful scope of the appended claims.

I claim:

1. A method of preparing alkali metal salts or alkaline earth metal salts of acyloxybenzenesulfonate by reacting an alkali metal salt or an alkaline earth metal salt of hydroxybenzenesulfonic acid with an organic compound containing olefinic unsaturation and carbon monoxide under an otherwise inert atmosphere at elevated temperature above about 125° C. and elevated pressure above about 500 psig in the presence of a catalytic amount of a metal carbonyl compound and a promoter selected from pyridine, non-ortho-substituted alkylpyridine or mixtures thereof.

2. The method of claim 1, wherein the olefinically unsaturated compound is selected from the group consisting of straight-chain alpha monoolefins, branched alphaolefins and aliphatic terminal diolefins having up to about 40 carbon atoms.

3. The method of claim 1, wherein the molar ratio of alkali metal salt or alkaline earth metal salt of hydroxybenzenesulfonic acid to olefinic unsaturated compound is 1:1.

4. The method of claim 1, wherein the metal carbonyl catalyst compound is selected from iron-pentacarbonyl, dicobaltoctacarbonyl or nickel-tetracarbonyl.

5. The method of claim 4, wherein the metal carbonyl compound is dicobalt-octacarbonyl.

6. A process of claim 1 wherein said metal carbonyl is iron carbonyl.

7. A process of claim 1 wherein said metal carbonyl is nickel carbonyl.

8. A process of claim 1 wherein said metal carbonyl is a cobalt carbonyl and said alkali metal salt or alkaline earth metal salt is a sodium salt.

9. The method of claim 8, wherein the amount of cobalt carbonyl compound present in the process is from about 1% to about 20% by weight based on the weight of the sodium salt of hydroxybenzenesulfonic acid reactant.

10. The method of claim 8, wherein the promoter is present in the process is an amount of from about 1-50 moles of promoter per mole of metal carbonyl compound.

11. The method of claim 8, wherein the non-ortho-substituted alkylpyridine is selected from 3-picoline, 4-picoline, 3,4-dimethylpyridine, 3,5-dimethylpyridine, 3-ethylpyridine and 4-ethylpyridine.

12. The method of claim 8, wherein the reaction is carried out at a temperature of from about 125° C. to about 200° C.

13. The method of claim 8, wherein the carbon monoxide pressure is from about 500 psig to about 4000 psig.

14. The method of claim 8, wherein a liquid solvent medium is present in the process.

15. The method of claim 14, wherein said solvent is acetonitrile.

16. The method of claim 14, wherein the solvent is isopropyl alcohol.

17. The method of claim 8, wherein the product produced by the process is benzenesulfonic acid, 4-hydroxynonanoate, sodium salt.

* * * * *